United States Patent [19]

Sakakibara et al.

[11] 4,261,885
[45] Apr. 14, 1981

[54] NOVEL SOMATOSTATIN ANALOGUE

[75] Inventors: Shunpei Sakakibara, Suita; Yukio Shigeta, Kobe, both of Japan

[73] Assignee: Shiraimatsu Shingaku Co., Ltd., Japan

[21] Appl. No.: 83,942

[22] Filed: Oct. 11, 1979

[30] Foreign Application Priority Data

Oct. 28, 1978 [JP] Japan .................................. 53-133055

[51] Int. Cl.$^3$ ............................................ C07C 103/52
[52] U.S. Cl. ............................................... 260/112.5 S
[58] Field of Search ................................. 260/112.5 S

[56] References Cited
U.S. PATENT DOCUMENTS 4,161,521 7/1979 Veber et al. ................... 260/112.5 S

OTHER PUBLICATIONS

Journal of the American Chemical Society, 98, (1976), 2367–2369.

*Primary Examiner*—Delbert R. Phillips
*Attorney, Agent, or Firm*—Wenderoth, Lind & Ponack

[57] ABSTRACT

Novel somatostatin analogs exhibiting high activity in inhibiting insulin glucagon and growth hormone secretion are depicted by the formula:

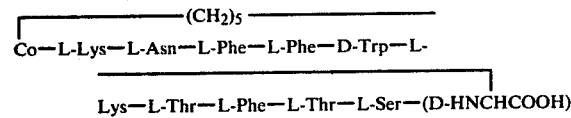

and pharmaceutically acceptable acid addition salts thereof.

2 Claims, 3 Drawing Figures

NOVEL SOMATOSTATIN ANALOGUE

BACKGROUND AND PRIOR ART

This invention is directed to a novel compound analogous to somatostatin, which is known as the peptidal release inhibiting factor and exhibits unusual biological activity in human beings and warm blooded animals. More particularly, it is directed to the undecapeptide represented by the following formula:

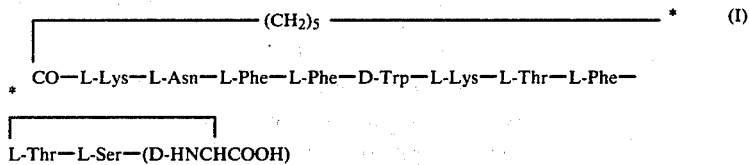

(I)

CO—L-Lys—L-Asn—L-Phe—L-Phe—D-Trp—L-Lys—L-Thr—L-Phe—

L-Thr—L-Ser—(D-HNCHCOOH)

Following the first isolation of somatostatin by Krulich in 1973, somatostatin has been demonstrated to inhibit the secretion of not only growth hormones but also insulin and glucagon, and in conjunction with the findings that an excess of glucagon plays in important role in causing diabetes and that growth hormones take part in the development of diabetic syndromes, efforts have been made to develop somatostatin derivatives which may strongly and specifically inhibit the secretion of glucagon and growth hormones.

The present invention has been made in furtherance of the above efforts and now provides the novel peptide of formula (I), tentatively designated by the inventors as Des-(Ala[1],Gly[2])-(D-Trp[8],D-Asu[3,14])-somatostatin, which exhibits unusual biological activities.

Independent of the inventors' investigation, a new synthetic peptide, the so-called DL-Asu-type somatostatin, was reported in the Journal of the American Chemical Society, Volume 98, page 2367, Apr. 14, 1976, in which its inhibiting activity for the release of growth hormones was disclosed to be only half that of somatostatin of natural origin. This very low activity was assumed by the inventors to be due to employment of optically inactive DL-α-aminosuberic acid as a starting material.

BRIEF DESCRIPTION OF THE INVENTION

On the basis of the findings that the N-terminal alanine[1] and glycine[2] together with the disulfide-linkage[3,14] in the structure of somatostatin are not required for manifesting biological activity and the disulfide-linkage is chemically very unstable, the inventors proposed partial conversion of the structure of somatostatin and in consequence, provide herewith the novel peptide represented by formula (I) which is characterized by the fact that all of the constituent amino acids are of the optically L-form except that trypsine[8] and α-aminosuberic acid[3,14] are of the optically D-form. This peptide is also characterized by its unusual biological activity and its stability, which is far superior to somatostatin itself when used in pharmaceutical preparations.

BRIEF DESCRIPTION OF THE DRAWINGS

FIG. 1-b is a graph depicting the same subject matter as FIG. 1-a except that the compound of this invention was employed in place of somatostatin.

FIG. 2-b is a graph depicting the same subject matter as FIG. 2-a except that the compound of this invention was employed in place of somatostatin.

FIG. 3-b is a graph depicting the same subject matter as FIG. 3-a except that the compound of this invention was employed in place of somatostatin.

Figure 1:
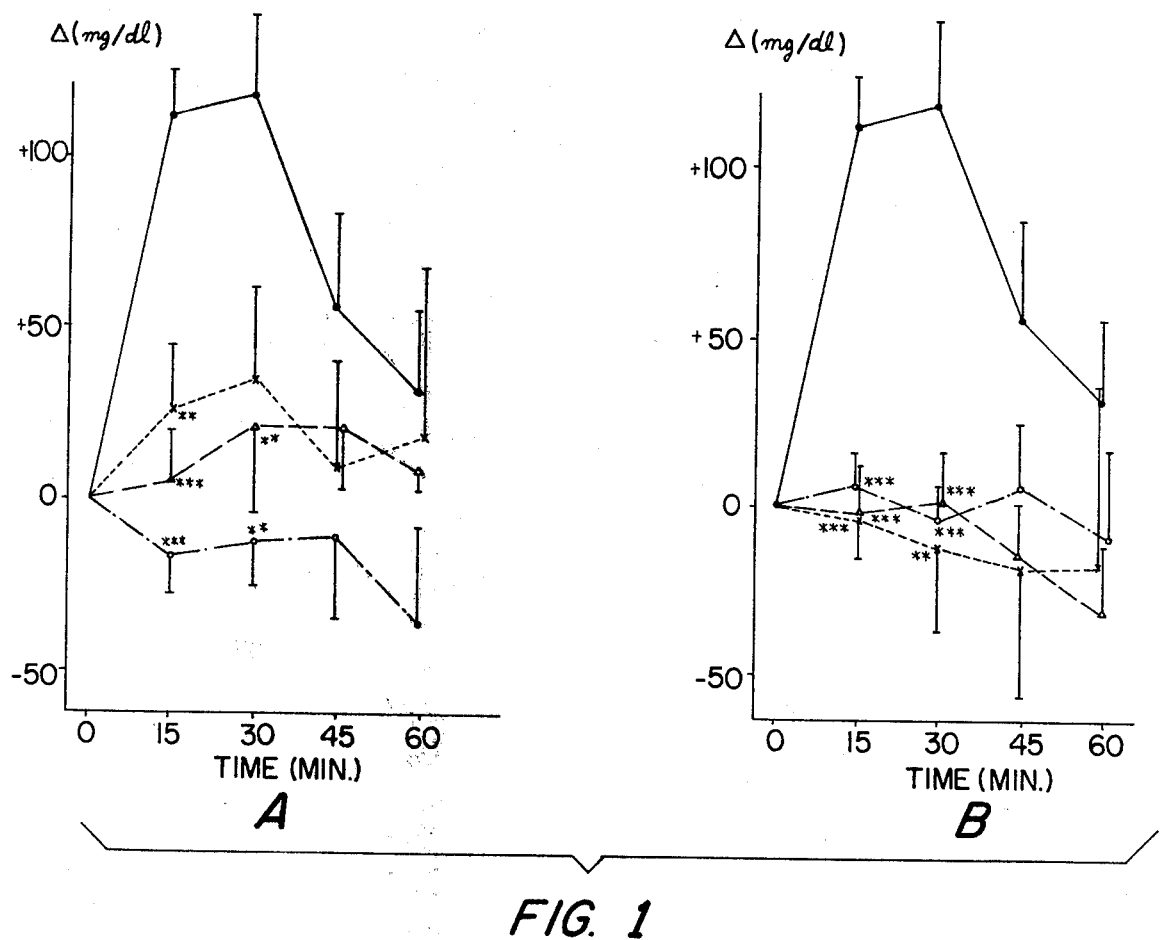
FIG. 1-a is a graph depicting the change in blood glucose level of rats which were stimulated by arginine (3 g/kg of body weight/hour) and infused with somatostatin, wherein the level of blood glucose (mg/dl) is expressed on the perpendicular axis and the time (minutes) is expressed on the horizontal axis.

In all of the Figures, •——• represents the control group, ✕----✕ represents the group administered the basal dose (4 μg/Kg of body weight/hour), o—•—o represents the group administered 10 times the basal dose and △----△ represents the group administered 100 times the basal dose, respectively.

The mark * represents $P<0.05$, the mark  represents $P<0.025$ and the mark * represents $P<0.01$.

DETAILED DESCRIPTION OF THE INVENTION

The following abbreviations, most of which are well known and commonly used in the art, are employed for the sake of convenience throughout the specification:
Ala—L-Alanine
Asn—L-Asparagine
Asp—L-Asparatic acid
Asu—α-Aminosuberic acid
Gly—L-Glycine
Lys—L-Lysine
Phe—L-Phenylalanine
Ser—L-Serine
Trp—Tryptophan
Thr—L-Threonine
Boc—t-Butoxycarbonyl
Bzl—Benzyl
AcOH—Acetic acid
Cbz(o-Cl)—o-Chlorobenzyloxycarbonyl
CHA—Cyclohexylamine
Cl-Ac—Chloroacetyl
DCHA—Dicyclohexylamine
DMF—Dimethylformamide
HOBT—1-Hydroxybenzotriazole
MeOH—Methylalcohol
OBzl—Benzyl ester
ONp—p-Nitrophenyl ester
OSu—N-Hydroxysuccinic-imido ester
OEt—Ethyl ester
TFA—Trifluoroacetic acid
THF—Tetrahydrofuran WSC—N-Ethyl-N'-dimethylaminopropyl-carbodiimide The undecapeptide of formula (I) can be prepared through various routes by employing techniques well known among synthetic peptide chemists of ordinary skill in the art, however, it is of course necessary to properly select a protecting group for the amino acids to be used. The protecting group of choice must be one which is stable both to reagents and under the conditions employed in succeeding steps of a reaction sequence.

Acute Toxicity:

The experiment for determining acute toxicity is carried out by infusing this compound into the tail vein of a test mouse in the amount of 5 mg/kg of body weight. No significant changes or side effects were observed in respect of body weight, body temperature and a blood sugar value. Consequently, the $LD_{50}$ value of this compound is considered to be insignificant.

The compound of formula (I) may be administered to warm-blooded mammals, including human beings, by any of several methods, including orally, subligually, subcutaneously, intramuscularly, intravenously and the like. As administration of this compound certainly inhibits the release of not only growth hormones but also insulin and glucagon, it is expected to be applicable for the analysis, diagnosis and treatment of diabetic conditions.

For the diagnosis of diabetic conditions, in place of the thus far employed somatostatin, which has been known to lower insulin sensitivity when applied to a primary diabetic condition, this compound is applicable in lower dosages than somatostatin itself because of its higher efficacy. For the treatment of diabetic conditions, such as control of unstable typed diabetes at its preoperative stage, diabetic ketoacidosis and diabetic malignant retinitis at its advanced stage, it is contemplated that the compound may be employed alone or be combined with insulin.

The inventors' tentatively recommended formula for administration in the treatment of the above-stated diabetic conditions is that, as a basal dose, about 4 mg of the compound per kg of a pateint's body weight being administered through a parenteral route over a period of one hour, however, it is evident that the dose range will vary widely depending upon the particular condition which is beint treated as well as the severity of the condition.

The compound of this invention can be used for pharmaceuticals in the form of pharmaceutically acceptable acid addition salts thereof, for example, with hydrochloric acid, acetic acid, tartaric acid, succinic acid, citric acid and the like.

Following examples are some of embodiments of this invintion:

Injections

The compound of this invention: 3.75 g
Sodium chloride: 90 g
Distilled water for injection: quantum sufficient The former two reagents are dissolved in 10 liters of the water, which are filtered under sterile conditions and are filled into ampoules in 1 ml portions.

Sublingual tablets:

The compound of this invention: 38 g
Crystalline cellulose: 322 g
White sugar: 69 g
Mannitol: 23 g
Perfume: 3.2 g These are combined and formed into 10,000 tablets each of 5 mm diameter and 45 mg weight according to the conventional methods in the art.

Aerosols:

The compound of this invention: 38 g
Dichlorofluoromethane: 500 ml
Perfume: quantum sufficient This is divided into 5 ml portions which are placed in a can according to the conventional methods in the art.

The following examples are illustrative of the preparation of the compound of this invention:

EXAMPLE I: Preparation of Boc-Ser(Bzl)-D-Asu-OBzl.CHA (1) Preparation of Boc-D-Asu-OBzl.DCHA D-Asu was prepared from Cl-Ac-DL-Asu by enzyme resolution, 13 g of thus obtained D-Asu ($[\alpha]_D^{25} -19.9°$ (C 3.1, 6 N HCl)) were dissolved in 100 ml of dioxane, which was allowed to stand with 25 g of S-t-butyloxycarbonyl-4,-dimethyl-2-mercaptopyrimidine and 82 ml of 2 N NaOH at room temperature for 24 hours. From the reaction mixture, dioxane was distilled off under reduced pressure and an excess of the reagents were removed by the extraction with ethyl ether. Then, the pH of the water layer was adjusted to 2–3 with 2 N HCl and the produced oily substance was extracted with ethyl acetate. The extracts were well washed with water, dried over $Na_2SO_4$, concentrated and were recrystallized from n-hexane, which gave 19.0 g (yield=95%) of Boc-D-Asu. m.p. 119°–122° C. $[\alpha]_D^{25} +15.1°$ (C 1.5, DMF). 18.0 g of thus obtained Boc-D-Asu were mixed with 8.7 ml of triethylamine, 20 ml of DMF and 6.7 ml of benzyl bromide and the mixture was allowed to stand at room temperature for 24 hours. The reaction product was added to an excess of water and the produced oily material was extracted with ethyl acetate. The extracts were well washed with water then with 5% aqueous $NaHCO_3$ solution and was extracted with 5% aqueous $Na_2CO_3$ solution three times. The water layer was made acidic with 6 N HCl and the produced oily material was again extracted with ethyl acetate. The extracts were well washed with water, then with 5% aqueous $NaHCO_3$ solution and was extracted with 5% aqueous $Na_2CO_3$ solution three times. The water layer was made acidic with 6 N HCl and the produced oily material was again extracted with ethyl acetate, washed with water and dried over $Na_2SO_4$. The ethyl acetate solution was exchanged with ethyl ether and was neutralized with the dropwise addition of DCHA under cooling. The resultant crystals were collected and washed with ethyl ether and recrystallized from methanol-ethyl ether, which gave 12.5 g (yield=34.5%) of the title compound. m.p. 80°–83° C. $[\alpha]_D^{25} +13.9°$ (C 1.8, DMF). Analysis—Calculated for $C_{32}H_{52}O_6N_2$: C, 68.52; H, 9.36; N, 5.00. Found: C, 68.53; H, 9.60; N, 4.95.

(2) Preparation of Boc-Thr(Bzl)-Ser(Bzl)-D-Asu-OBzl.CHA

In ethyl acetate, were suspended 12.0 g of Boc-D-Asu-OBzl.DCHA obtained from the preceding step (1) and the suspension was treated with 1 N $H_2SO_4$ to remove DCHA from the compound. The organic layer was washed, dried over $Na_2SO_4$ and concentrated, and the oily material produced. The material was dissolved in 20 ml of TFA and was allowed to stand at room temperature for 45 minutes. An excess of TFA was removed by distillation under reduced pressure and the produced oily material was dissolved in 20 ml of DMF and neutralized with triethylamine. Then 10.0 g of Boc-Ser(Bzl)-Osu and 0.2 g of HOBT were added to the neutralized solution under cooling at 0° C., which was stirred at 0° C. for 4 hours then at room temperature for 20 hours. To the reaction mixture, 1 ml of dimethylpropanediamine was added to inactivate an excess of the active ester, then 200 ml of ethyl acetate was added and the organic layer was well washed successively with 1 N HCl, water, 5% aqueous $NaHCO_3$ solution and water then dried over $Na_2SO_4$, concentrated and the organic layer was dissolved in ethyl ether. The ether solution was neutralized with the dropwise addition of CHA and the resultant crystals were collected, washed with ethyl ether and recrystallized from ethyl acetate-n-hexane, which gave 8.5 g (yield=62%) of Boc-Ser(Bzl)-D-Asu-OBzl.CHA. m.p. 104°–106° C. $[\alpha]_D^{25} + 9.5°$ (C 1.3, DMF). Analysis—Calculated for $C_{36}H_{53}O_8N_3$: C, 65.91; H, 8.16; N, 6.41. Found: C, 66.18; H, 8.27; N, 6.35.

To a suspension of 7.0 g of thus prepared Boc-Ser(Bzl)-D-Asu-OBzl.CHA in 100 ml of ethyl acetate, 1 N HCl was added and the mixture was layer-separated to remove CHA from the compound. The organic layer was washed with water, dried over $Na_2SO_4$ and the oily material produced, which was dissolved in 30 ml of TFA, was allowed to stand for 45 minutes at room temperature. An excess of TFA was distilled off in vacuo and the produced oily material was dissolved in 20 ml of DMF and neutralized with triethylamine, to which 5.2 g of Boc-Thr(Bzl)-Osu and 0.2 g of HOBT were added and the mixture was then subjected to stirring for 2 hours at 0° C. and for 20 hours at room temperature, to which 1 ml of dimethylpropanediamine was added for inactivating an excess of the active ester. 100 ml of ethyl acetate were added to the reaction solution and the separated organic layer was washed successively with 1 N HCl, Water, 5% aqueous $NaHCO_3$ solution and water, dried over $Na_2SO_4$, concentrated and then was dissolved in ethyl ether. To the ether layer, CHA was added dropwise for neutralization. The resultant crystals were collected and washed with ether, then recrystallized from ethyl acetate-n-hexane, which gave 7.3 g (yield=82%) of the title compound. m.p. 120°–126° C. $[\alpha]_D^{25} + 16.9°$ (C 1.8, DMF). Analysis—Calculated for $C_{47}H_{66}O_{10}N_4 \cdot \frac{3}{4}H_2O$: C, 65.59; H, 7.91; N, 6.51. Found: C, 65.86; H, 7.94; N, 6.59.

EXAMPLE II: Preparation of Boc-D-Trp-Lys[Cbz(o-Cl]-Thr(Bzl)-Phe-NHNH₂

(1) Preparation of Boc-Thr(Bzl)-Phe-OEt

To 200 ml of methylene chloride, were added 31.0 g of Boc-Thr(Bzl)-OH and 27.6 g of Phe-OEt.HCl, and 18.3 ml of WSC were added to the mixture under cooling at 0°—5° C., which was then subjected to stirring for 2 hours at 0°—5° C. then for 18 hours at room temperature. The methylene chloride in the reaction solution was exchanged with ethyl acetate and the exchanged solution was washed successively with 1 N HCl, 5% aqueous $NaHCO_3$ solution and water and dried over $MgSO_4$. The organic layer was concentrated and the produced material was crystallized from hexane, which gave 39.0 g (yield=81%) of the title compound. m.p. 99°–100.5° C. $[\alpha]_D^{25} + 6.2°$ (C 2.7, DMF). Analysis—Calculated for $C_{27}H_{36}O_6N_2$: C, 66.92; H, 7.49; N, 5.78. Found: C, 66.91; H, 7.57; N, 5.75.

(2) Preparation of Boc-Lys[Cbz(o-Cl)]-Thr(Bzl)-Phe-OEt

In TFA were dissolved 14.6 g of Box-Thr(Bzl)-Phe-OEt obtained from the preceding step (1) and the solution was allowed to stand for 45 minutes at room temperature. An excess of TFA was distilled off in vacuo, to which n-hexane was added to produce a precipitate, which was collected and dried in a dessicator over NaOH in vacuo. The dried material was dissolved in 30 ml of DMF, which was neutralized with 4.2 ml of triethylamine. Then 24 g of Boc-Lys[Cbz(o-Cl)]-ONp were added under cooling and this was allowed to stand for 1 hour at 0° C. then for 72 hours at room temperature. 1 ml of dimethylpropanediamine was added to the reaction mixture to inactivate an excess of the active ester, to which 200 ml of ethyl acetate were added and the mixture was washed in turn with 1 N HCl, water, 5% aqueous $NaHCO_3$ solution and water and was then dried over $MgSO_4$. The organic layer was concentrated in vacuo and made to crystallize with n-hexane. The collected crystals were recrystallized from methanol-n-hexane, which gave 17.0 g (yield=73%) of the title compound. m.p. 96°–98° C. $[\alpha]_D^{25} + 2.7°$ (C 1.7, DMF). Analysis—Calculated for $C_{41}H_{53}O_9N_4Cl$: C, 63.02; H, 6.84; N, 7.17. Found: C, 62.76; H, 6.90; N, 7.16.

(3) Preparation of Boc-D-Trp-Lys[Cbz(o-Cl)]-Thr(Bzl)-Phe-OEt

In 30 ml of TFA were dissolved 15.6 g of Boc-Lys[Cbz(o-Cl)]-Trh(Bzl)-Phe-OEt obtained from the preceding step (2) and the solution was allowed to stand for 45 minutes at room temperature. After an excess of TFA was distilled off in vacuo, a precipitate was produced by adding ethyl ether. This was collected and dried over NaOH in a dessicator. The material was dissolved in 30 ml of DMF and was neutralized with triethylamine, to which 10 g of Boc-D-Trp-Osu and 1 g of HOBT were added under cooling at 0° C. The reaction solution was allowed to stand for 2 hours at 0° C. then for 48 hours at room temperature, to which 200 ml of $CHCl_3$ was added and the mixture was washed successively with 5% aqueous $NaHCO_3$ solution, water, 1 N HCl and water, and dried over $MgSO_4$. The organic layer was distilled off and the residue was treated with chloroform-ethyl ether-n-hexane, which gave 16.1 g (yield=81%) of the title compound. m.p. 105°–108° C. $[\alpha]_D^{25} + 11.7°$ (C 1.8, DMF). Analysis—Calculated for $C_{52}H_{63}O_{10}N_6Cl \cdot H_2O$: C, 63.37; H, 6.65; N, 8.53. Found: C, 63.28; H, 6.56; N, 8.50.

(4) Preparation of Boc-D-Trp-Lys[Cbz(o-Cl)]-Thr(Bzl)-Phe-NHNH₂

In 45 ml of the mixture of DMF:MeOH=2:1, were dissolved 15 g of Boc-D-Trp-Lys[Cbz(o-Cl)]-Thr(Bzl)-Phe-OEt obtained from the preceding step (3), to which hydrazine hydrate (80%) was added. This was allowed to stand for 5 hours at room temperature. The resultant precipitate was suspended in ethyl acetate and was collected by filtration and was well washed with ethyl acetate. The material was suspended in methanol, which was warmed until it became clear and was cooled. Then precipitation occurred from the cooled solution by adding water. The precipitate was collected, washed with ethyl ether, then with ethyl acetate and was dried in vacuo, which gave 14.0 g (yield=96%) of the title compound. m.p. 162°-164° C. $[\alpha]_D^{25}+8.3°$ (C 1.7, DMF). Analysis—Calculated for $C_{50}H_{61}O_9N_8Cl$: C, 62.97; H, 6.46; N, 11.75. Found: C, 62.71; H, 6.52; N, 11.88.

EXAMPLE III: Preparation of Boc-D-Trp-Lys[Cbz(o-Cl)]-Thr(Bzl)-Phe-Thr(Bzl)-Ser(Bzl)-D-Asu-OBzl [Condensation of the compounds obtained from Example I and Example II]

In 100 ml of ethyl acetate were added 7.0 g of Boc-Thr-(Bzl)-Ser(Bzl)-D-Asu-OBzl.CHA obtained from Example 1, from which CHA was removed by treating with 1 N HCl. The organic layer was well washed with water, dried over MgSO₄ and concentrated in vacuo. The residue was dissolved in 20 ml of TFA and the solution was allowed to stand for 45 minutes at room temperature. Then an excess of TFA was distilled off in vacuo and the resultant oily material was dissolved in DMF, which was neutralized with triethylamine under cooling, to which water was added to produce an oily material again. The oily material was dissolved in methanol, which was concentrated and dehydrated by an azeotropic distillation with benzene. The residue was dissolved in 5 ml of DMF and the solution was cooled to −10° C. to produce a DMF solution of H-Thr(Bzl)-Ser(Bzl)-D-Asu-OBzl.

On the other hand, 8.0 g of Boc-D-Trp-Lys[Cbz(o-Cl)]-Thr(Bzl)-Phe-NHNH₂ obtained from Example II was dissolved in 15 ml of DMF, to which 6.9 ml of 5.4 N HCl solution of dioxane was added under cooling at −15° C. and 1.25 ml of isoamylnitrite was added to the mixture under vigorous stirring at −15° C. and the mixture was allowed to stand for 10 minutes. The reaction mixture was neutralized with triethylamine and it was combined with the above-prepared DMF solution of H-Thr(Bzl)-Ser(Bzl)-D-Asu-OBzl. The combined solution was allowed to stand for 48 hours at −10° C., to which cooled 5 N H₂SO₄ was added and then precipitation occurred. The collected precipitate was washed with water and dried in a dessicator. The dried material was suspended in methanol, which was warmed until it became clear and then was cooled to cause crystallization. The resultant crystals were recrystallized from ethyl acetate-n-hexane, which gave 7.5 g (yield=58%) of the title compound. m.p. 151°-161° C. (decomposition). $[\alpha]_D^{25}+24.5°$ (C 0.6, DMF). Analysis—Calculated for $C_{86}H_{102}O_{17}N_9Cl.2H_2O$: C, 64.33; H, 6.67; N, 7.85. Found: C, 64.64; H, 6.43; N, 7.69. Amino acid analysis: Lys 1.05(1), Thr 2.02(2), Ser 0.93(1), Phe 1.00(1), Asu 1.09(1), Trp 0.19(1).

In this invention, the amino acid analysis was performed by adding 6 N HCl containing a few drops of anisole to the subject peptide and the mixture was hydrolyzed for 24 hours at 108° C. Then the resulting solution was evaporated to dryness in vacuo, the residue of which was subjected to analysis.

EXAMPLE IV: Preparation of Boc-Lys[Cbz(o-Cl)]-Asn-Phe-Phe-OEt.

(1) Preparation of Boc-Phe-Phe-OEt

In 150 ml of chloroform were dissolved 26.5 g of Boc-Phe-OH and 22.9 g of H-Phe-OEt.HCl, to which 18.4 ml of WSC was added under cooling at 0° C. This was then subjected to stirring for 2 hours at −10° C., then 15 hours at room temperature. The reaction solution was concentrated in vacuo and the residue was dissolved in 20 ml of ethyl acetate, washed successively with 1 N HCl, water, 5% aqueous NaHCO₃ solution and water, dried over Na₂SO₄ then again concentrated in vacuo. The thus obtained residue was added to n-hexane and the resultant amorphous precipitate was collected, and was recrystallized from n-hexane, which gave 37 g (yield=84%) of the title product. m.p. 106.5°-107.5° C. $[\alpha]_D^{25}-9.7°$ (C 1.3, DMF). Analysis—Calculated for $C_{25}H_{32}O_5N_2$: C, 68.16; H, 7.32; N, 6.36. Found: C, 67.85; H, 7.32; N, 6.49.

(2) Preparation of Boc-Asn-Phe-Phe-OEt

In 35 ml of TFA was dissolved 8.2 g of Boc-Phe-Phe-OEt, and the solution was allowed to stand for 35 minutes at room temperature and an excess of TFA was distilled off in vacuo. Ether was added to the solution. Then the resultant precipitate was collected and dried over NaOH in vacuo in a dessicator. The dried material was dissolved in 25 ml of DMF, to which 10.6 g of Boc-Asn-ONp and 1 g of HOBT were added. The solution was stirred for 2 hours at 0° C. and for 20 hours at room temperature, after which a large quantity of water was added. Then precipitation occurred, which precipitate was collected and washed with water, then with ethyl ether. It was crystallized from methanol-ethyl ether and further recrystallized from methanol, which gave 8.0 g (yield=73%) of the title product. m.p. 188°-189° C. $[\alpha]_D^{25}-31.7°$ (C 1.1, DMF). Analysis—Calculated for $C_{29}H_{38}O_7N_4$: C, 62.80; H, 6.91; N, 10.10. Found: C, 62.93; H, 6.93; N, 10.21.

(3) Preparation of Boc-Lys[Cbz(o-Cl)]-Asn-Phe-Phe-OEt

In 25 ml of TFA were dissolved 5.5 g of Boc-Asn-Phe-Phe-OEt obtained from the preceding step (2), which was treated for 35 minutes at room temperature and an excess of TFA was distilled off in vacuo. Ethyl ether was added to the residue and the resultant precipitate was collected and dried over NaOH in a dessicator in vacuo. The material was dissolved in 20 ml of DMF, which was neutralized with 14 ml of triethylamine and 7 g of Boc-Lys[Cbz(o-Cl)]-ONp and 0.5 g of HOBT were added to the neutralized solution under cooling at 0° C., which was allowed to stand for 2 hours then 20 hours at room temperature, to which a large quantity of water was added. The resultant precipitate was collected and washed with water and then ethyl ether and was crystallized from methanol, which gave 7.0 g (yield=86%) of the title product. m.p. 179°-181° C. $[\alpha]_D^{25}-30.8°$ (C 1.0, DMF). Analysis—Calculated for $C_{43}H_{55}O_{10}N_6Cl$: C, 60.66; H, 6.51; N, 9.87. Found: C, 60.30; H, 6.47; N, 9.76.

(4) Preparation of Boc-Lys[Cbz(o-Cl)]-Asn-Phe-Phe-NHNH₂

To the mixture of 20 ml of DMF and 30 ml of methanol was added 5.6 g of Boc-Lys[Cbz(o-Cl)]-Asn-Phe-Phe-OEt obtained from the preceding step (3), to which 6.6 ml of hydrazine hydrate (80%) was added and the mixture was allowed to stand for 48 hours at room temperature. The resulting solution was concentrated in vacuo, to which a large quantity of water was added and the resulting precipitate was collected, which was reprecipitated from DMF-water, which gave 4.1 g (yield=70%) of the title product. m.p. 212°-213° C. (decomposition). $[\alpha]_D^{25}-38.9°$ (C 1.05, DMF). Analysis—Calculted for $C_{41}H_{53}O_9N_8Cl$: C, 58.88; H, 6.27; N, 13.39. Found: C, 58.45; H, 6.41; N, 13.10.

EXAMPLE V: Preparation of Boc-Lys[Cbz(o-Cl)]-Asn-Phe-Phe-D-Trp-Lys[Cbz(o-Cl)]-Thr(Bzl)-Phe-Thr(Bzl)-Ser(Bzl-D-Asu-OBzl [Condensation of the compounds obtained from Example III and Example IV]

In 35 ml of TFA solution containing 3.5 ml of dimethylsulfide and 1 ml of ethanedithiol were dissolved 6.5 g of Boc-D-Trp-Lys[Cbz(o-Cl)]-Thr(Bzl)-Phe-Thr(Bzl)-Ser(Bzl)-D-Asu-OBzl which was obtained from Example III and the mixture was allowed to stand for 45 minutes at room temperature. An excess of TFA was distilled off and ethyl ether was added to the residue and the resulting precipitate was collected and dissolved in 20 ml of DMF, which was neutralized with triethylamine under cooling, to which an excess of water was added and the resulting precipitate was collected, washed with water then with ethyl ether and dried in a dessicator over NaOH in vacuo. The dried material was dissolved in 5 ml of DMF, which was cooled to $-10°$ C. then the DMF solution of H-D-Trp-Lys[Cbz(o-Cl)]-Thr(Bzl)-Phe-Thr(Bzl)-Ser(Bzl)-D-Asu-OBzl was produced.

On the other hand, 3.5 g of Boc-Lys[Cbz(o-Cl)]-Asn-Phe-Phe-NHNH$_2$ obtained from Example IV was dissolved in 15 ml of DMF, to which 3.5 ml of 5.4 N HCl-dioxane was added under cooling at $-15°$ C. and 0.5 ml of isoamylnitrite were added to the mixture. 10 minutes later, triethylamine was further added at $-15°$ C., to which the preceding DMF solution was added and the mixture was allowed to stand for 48 hours at $-10°$ C. A large quantity of water was added to the reaction solution and the resulting precipitate was collected, washed with methanol, then was reprecipitated with methanol, which gave 6.6 g (yield=70%) of the title product. m.p 208°-214° C. (decomposition). $[\alpha]_D^{25}+3.5°$ (C 0.6, DMF). Analysis—Calculated for $C_{122}H_{143}O_{24}N_{15}Cl_2 \cdot H_2O$: C, 63.90; H, 6.39, N, 9.17. Found: C, 63.80; H, 6.40; N, 9.39. Amino acid analysis: Lys 2.06(2), Asp 1.00(1), Thr 2.04(2), Ser. 0.85(1), Phe 2.90(3), Asu 0.92(1), Trp (positive to the Ehrlich reaction).

EXAMPLE VI: Preparation of Boc-Lys[Cbz(o-Cl)]-Asn-Phe-Phe-D-Trp-Lys[Cbz(o-Cl)]-Thr(Bzl)-Phe-Thr(Bzl)-Ser

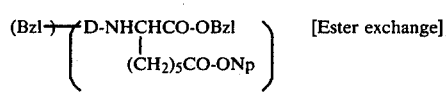

[Ester exchange]

In 50 ml of dried pyridine was dissolved 5.4 g of Boc-Lys[Cbz(o-Cl)]-Asn-Phe-Phe-D-Trp-Lys[Cbz(o-Cl)]-Thr(Bzl)-Phe-Thr(Bzl)-Ser(Bzl)-D-Asu.OBzl obtained from the preceding Example V, to which 7.0 g of TFA-ONp were added, and the mixture was allowed to stand for 3 hours at 50° C. to cause transesterification. Pyridine was distilled off in vacuo from the reaction solution and ethyl ether was added to the residue, then the resulting precipitate was collected, washed with ether and reprecipitated with DMF-ethyl ether, which gave 5.0 g (yield=87%) of the title product. m.p. 215°–255° C. (decomposition). $[\alpha]_D^{25}+5.3°$ (C 0.6, DMF). Analysis—Calculated for $C_{128}H_{146}O_{26}N_{16}Cl_2 \cdot H_2O$: C, 63.27; H, 6.15; N, 9.22. Found: C, 62.97; H, 6.11; N, 9.32.

EXAMPLE VII: Preparation of

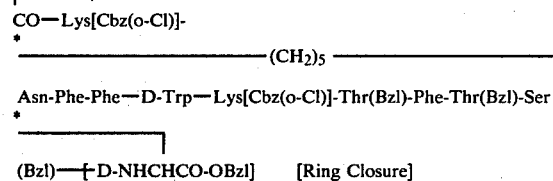

[Ring Closure]

In 30 ml of TFA which contained 2 ml of dimethylsulfide and 1 ml of ethanedithiol were dissolved 4.5 g of Boc-Lys[Cbz(o-Cl)]-Asn-Phe-Phe-D-Trp-Lys[Cbz(o-Cl)]-Thr(Bzl)-Phe-Thr(Bzl)-Ser(Bzl)-D-

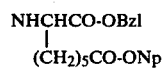

obtained from Example VI. The mixture was allowed to stand for 45 minutes at room temperature. An excess of TFA was distilled away in vacuo from the reaction solution and the resulting residue was dissolved in 50 ml of DMF, which was poured dropwise into 1.9 liters of pyridine over 1 hour at 50° C. The solution was stirred for 24 hours at 50° C. and was concentrated in vacuo to remove pyridine. The residue was added to 0.5 N HCl and the resulting precipitate was washed with water, then with ethyl ether and was repredipitated from DMF-ethyl ether, which gave 2.7 g (yield=68%) of the title product. m.p. 135°-145° C. $[\alpha]_D^{25}+2.1°$ (C 0.6, DMF). Analysis—Calculated for $C_{117}H_{133}O_{21}N_{15}Cl_2 \cdot 3H_2O$: C, 63.56; H, 6.35; N, 9.50. Found: C, 63.46; H, 6.11; N, 9.54.

EXAMPLE VIII: Preparation of

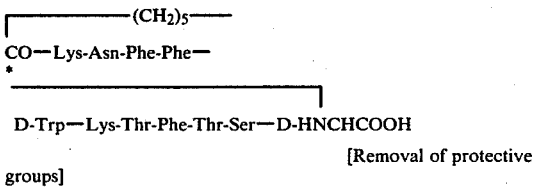

[Removal of protective groups]

In 20 ml of anhydrous HF were dissolved 3 ml of anisole, 2 ml of dimethylsulfide and 1.5 g of the product obtained from Example VII and the mixture was allowed to stand for 60 hours at 0° C. An excess of HF was distilled off and the resulting residue was washed with ethyl ether and then was dried over NaOH in a dessicator, which gave a pale yellow powder. The powder was dissolved in 50% acetic acid then the solution was diluted to form a 5% acetic acid solution. The resulting precipitate was centrifugally removed and the effluent was lyophilized to dryness, which gave 810 mg of hydrochloride of the crude title product. The crude material was dissolved in 2 M acetic acid and the solution was poured into a Sephadex LH-20 column (3.5 cm×135 cm), which was treated with 2 M acetic acid and the active fraction of the effluent was lyophilized to dryness. 140 mg of the lyophilized material was refined by partition chromatography on a Sephadex G-25 column (3 cm×50 cm) using as a developing solvent the mixture of n-butanol:acetic acid:water=4:1:5. The active fraction of the effluent was concentrated to remove the organic solvent and the resulting residue was lyophilized to dryness, which was again applied to a Sephadex LH-20 column (2 cm×100 cm) using with 2 N acetic acid and was lyophilized to dryness, which gave 50 mg of the title product.

Amon acid analysis: Lys 2.05(2), Asp 1.09(1), Thr 2.02(2), Ser 0.87(1), Phe 3.00(3), Asu 1.00(1), $NH_3$ 1.82(1), Trp 0.95(1)*. Note: * was determined by spectroscopy.

The product of this invention is a white powder and is soluble in water. It shows a single spot by thin layer chromatography with an Rf value of 0.51 (solvent system n-butanol:acetic acid:water=4:1:5, supernatant layer) and an Rf value of 0.80 (Solvent system n-butanol:acetic acid:water:pyridine—30:6:24:20), respectively. Paper electrophoresis (pH 4.8, 1500 V, 60 minutes). Optical rotation $[\alpha]_D^{30}$ —43.5° (C 0.25, 1% acetic acid).

Pharmacological properties:

Studies were made of the effects of the compound of this invention on arginine-induced changes in blood glucose, insulin and glucagon levels and the results obtained were compared with those of somatostatin.

Method

Male SD rats weighing 300 to 500 g were anesthetized with sodium pentobarbital (60 mg/kg of body weight, by intraabdominal puncture) and polyethylene catheters were placed in their carotid artery. Saline was infused over 10 minutes, and arginine was infused at a rate of 3 g/kg/hr, for 60 minutes, using an infusion pump (at a rate of 4.5 ml/kg/hr). For 30 minutes, immediately after the start of arginine infusion, somatostatin or the compound of this invention was infused at rates of 4 μg/kg/hr, as a basal dose, 40 μg/kg/hr as 10 times as the basal dose, and 400 μg/kg/hr, as 100 times as the basal dose, respectively.

Before and 15 minutes, 30 minutes and 60 minutes after the start of arginine infusion, blood samples were taken in the presence of heparine. Blood glucose values were measured by the glucose oxidase method, and blood insulin and glucagon values were measured by the radioimmunoassay method.

Results

After the start of arginine infusion, at the rate of 3 g/kg/hr, there was a rise in blood glucose levels that reached a peak in 30 minutes and thereafter gradually descended. The rise in blood glucose levels was inhibited by the addition of somatostatin. Statistically significant low levels of blood glucose were shown with the addition of somatostatin, at more than 10 and 100 times the basal dose, 15 minutes and 30 minutes after the start of arginine infusion, respectively (refer to the attached FIG. 1-*a*).

Figure 2:
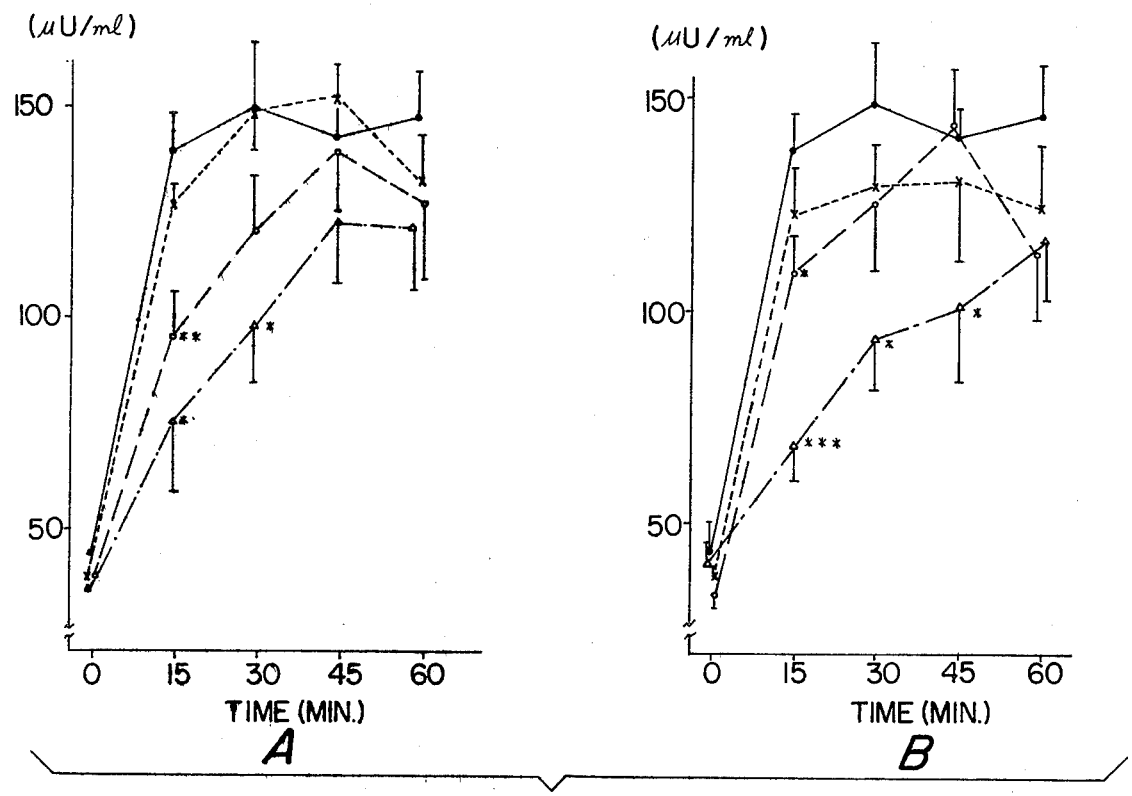
FIG. 2-a is a graph depicting the changes of blood insulin-antibody level (IRI) on rats treated as discussed above with regard to FIG. 1-a, wherein IRI levels (μU/ml) are expressed on the perpendicular axis and the time (minutes) is expressed on the horizontal axis.

With the infusion of the compound of this invention, at more than the basal dose, lower blood glucose levels than those of the control were obtained 15 minutes and 30 minutes after the start of arginine infusion (refer to the attached FIG. 1-*b*). Arginine raised blood insulin level, which remained almost unchanged 15 minutes after the start of arginine infusion. Somatostatin inhibited the rise in blood insulin levels dose dependently (refer to the attached FIG. 2-*a*). 15 minutes and 30 minutes after the start of arginine infusion, the rise in blood insulin levels was significantly inhibited by somatostatin at more than 10 times the basal dose and at more than 100 times the basal dose, respectively (refer to the attached FIG. 2-*b*). Notably, 45 minutes after the start of arginine infusion, somatostatin failed to exert its effect and blood insulin level was raised again and returned to the control level. On the other hand, the compound of this invention still exerted its effect 15 minutes after the suspension of its infusion, and at 100 times the basal dose, blood insulin showed significantly lower levels as compared to the control (P>0.05).

Figure 3:
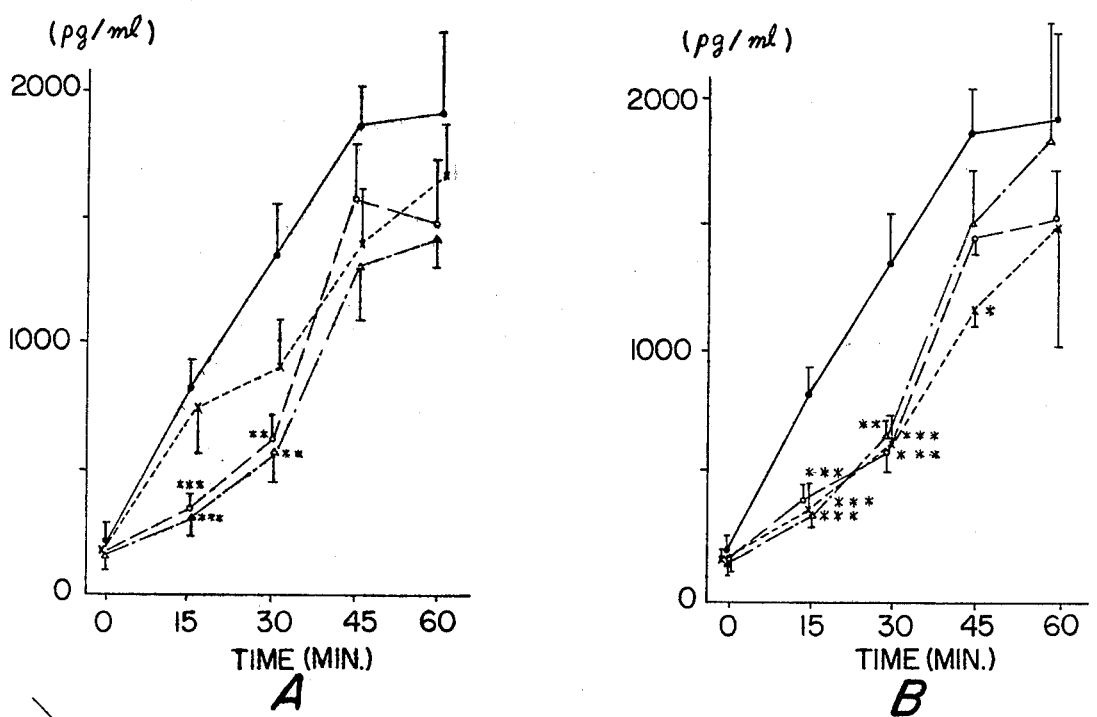
FIG. 3-a is a graph depicting the change of blood glucagon-antibody level (IRG) on rats treated as same as in FIG. 1-a, wherein the IRG level (pg/ml) is expressed on the perpendicular axis and the time (minutes) is expressed on the horizontal axis.

Blood glucagon levels were also raised with the infusion of arginine. Somatostatin at more than 10 times the basal dose significantly lowered its level 15 minutes and 30 minutes after the start of arginine infusion but lost its effect 45 minutes after (refer to the attached FIG. 3-*a*).

The compound of this invention significantly inhibits the rise in glucagon levels at the basal dose as well as at 10 and 100 times the basal dose, 15 minutes and 30 minutes after the start of arginine infusion, as compared to the control (refer to the attached FIG. 3-*b*). 45 minutes after the start of arginine infusion, blood glucagon levels rose again, however, significantly low values of glucagon antibody were observed with the compound of this invention at the basal dose as compared to the control.

Conclusion

The compound of this invention, like somatostatin, inhibited the blood insulin and glucagon secretions enhanced by arginine, and at the same time, inhibited the rise in blood glucose levels. The compound of this invention inhibited the blood insulin secretion to a similar extent as somatostatin, and inhibited the blood glucagon secretion. Its pharmacological activity was recognized to be more than 10 times or more that of somatostatin. While with somatostatin, 15 minutes afer the suspension of infusion, its effect was no longer observed, the compound of this invention retained its effect after the suspension of its infusion. Thus, it was suggested that the duration of activity of this compound was longer than that of somatostatin.

What we claim is:

1. A compound of the formula:

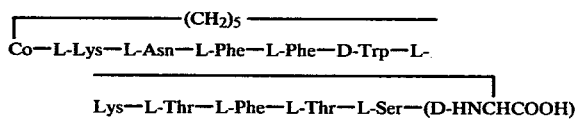

and pharmaceutically acceptable acid addition salts thereof.

2. The compound in accordance with claim 1, wherein pharmaceutically acceptable acid addition salts are selected from the group consisting of hydrochloric acid, acetic acid, tartaric acid, succinic acid and citric acid.

* * * * *